US005750410A

United States Patent [19]

Dou et al.

[11] Patent Number: 5,750,410
[45] Date of Patent: May 12, 1998

[54] METHOD OF AND APPARATUS FOR IMMUNE ANALYSIS

[75] Inventors: Xiaoming Dou; Yoshinori Yamaguchi; Harumi Uenoyama, all of Kyoto, Japan

[73] Assignee: Kyoto Dai-ichi Kagaku Co., Ltd., Kyoto, Japan

[21] Appl. No.: 592,522

[22] Filed: Jan. 26, 1996

[51] Int. Cl.[6] .................................................. G01N 33/553
[52] U.S. Cl. .................... 436/525; 422/82.05; 422/82.09; 422/82.11; 435/962; 436/154; 436/524; 436/536
[58] Field of Search ...................... 422/82.05, 82.09, 422/82.11; 435/962; 436/525, 164, 524, 536

[56] References Cited

U.S. PATENT DOCUMENTS

| | | |
|---|---|---|
| 4,208,185 | 6/1980 | Sawai et al. ........................ 23/230 B |
| 5,112,129 | 5/1992 | Carrabba et al. ........................ 356/301 |
| 5,376,556 | 12/1994 | Tarcha et al. ........................ 436/525 |
| 5,468,644 | 11/1995 | Stephenson et al. ........................ 436/163 |
| 5,607,643 | 3/1997 | Xiaoning et al. ........................ 422/82.05 |

FOREIGN PATENT DOCUMENTS

| | | |
|---|---|---|
| 254 430 | 1/1988 | European Pat. Off. . |
| 654 670 A3 | 5/1995 | European Pat. Off. . |
| 2 691 546 | 11/1993 | France . |

*Primary Examiner*—Carol A. Spiegel
*Attorney, Agent, or Firm*—Nikaido Marmelstein Murray & Oram LLP

[57] ABSTRACT

A total reflection cell has a total reflection prism on at least one surface thereof. A mixed solution containing a gold colloid labelled antibody which is adsorbed on a gold colloid is stored in the total reflection cell, and a sample solution containing an antigen causing antigen-antibody reaction with the antibody is added thereto for forming a gold colloid labelled immune complex. A measuring beam is introduced into the total reflection prism from an incident optical system at an angle θ of incidence causing total reflection and an outgoing beam from the total reflection prism is received by a measuring optical system, thereby measuring absorption by the gold colloid labelled immune complex and carrying out qualification and determination of the antigen.

5 Claims, 12 Drawing Sheets

METHOD OF AND APPARATUS FOR IMMUNE ANALYSIS

BACKGROUND OF THE INVENTION

1. Field of the Invention

The present invention relates to a method of and apparatus for immunologically analyzing an object of measurement in the field of clinical testing, biochemical sample measurement, quality control of drugs and the like.

2. Description of the Background Art

Immunological analysis methods employing antigen-antibody reaction include fluorescent immunoassay and luminous immunoassay. In any one of these methods, an antigen which is labeled with a fluorescent material or a chemiluminescent material is reacted to an antibody with an antigen which is an object of measurement in competition, to form an immune complex which is a molecular complex by the antigen-antibody reaction for measuring fluorescence or luminescence from the label, thereby quantitatively analyzing the target material.

On the other hand, a method of adding an antigen or an antibody of an object of measurement to an antibody or an antigen and measuring absorption or scattering of light by an immune complex which is formed by antigen-antibody reaction thereby making quantitative analysis is known as an optical measuring method utilizing neither fluorescence nor luminescence. Quantitative analysis methods utilizing light scattering phenomenons include turbidimetry and nephelometry. The former is adapted to measure transmitted light which is attenuated by absorption and scattering, while the latter is adapted to measure scattering light intensity. The method by light scattering is adapted to measure Rayleigh scattering or Mie scattering, in response to sizes of particles as measured.

A fluorescent immunoassay apparatus belonging to fluorescent immunoassay is proposed as an immunoassay apparatus employing a total reflection cell (refer to Japanese Patent Laying-Open Gazette No. 5-203574 (1993)). In this fluorescent immunoassay, an antibody is fixed to a surface of a total reflection prism, an antigen contained in a sample is bonded to the antibody by antigen-antibody reaction, and an antibody which is labelled with a fluorescent material is further bonded to the antigen by antigen-antibody reaction. Thereafter B-F separation is performed to remove an unreacted antibody which is labelled with the fluorescent material, and then an excitation beam is introduced into the total reflection prism to excite the labelled antigen-antibody immune complex which is constrained on the surface of the total reflection prism, for measuring fluorescence generated from the fluorescent material.

The method utilizing light scattering, which is homogeneous immunoassay, is a simple method requiring neither B-F separation nor washing. However, the method utilizing Rayleigh scattering or Mie scattering has problems of low detection sensitivity and low measuring accuracy in relation to a low concentration material.

On the other hand, the fluorescent or luminescent immunoassay requires complicated chemical treatment for labelling an antigen or an antibody with a fluorescent or chemiluminescent material. Further, most thereof is heterogeneous immunoassay, which inevitably requires B-F separation for separating an immune complex (B) making antigen-antibody reaction from an antigen or antibody (F) making no antigen-antibody reaction and washing through a large number of analytical steps.

SUMMARY OF THE INVENTION

The inventors have made deep study in order to qualitatively and quantitatively analyze an immune complex by absorption measurement of the immune complex, to discover that absorption of the immune complex can be measured in excellent sensitivity when the immune complex is brought into a state adsorbed by noble metal colloidal particles, although no absorption having sensitivity suitable for measurement can be obtained from the immune complex itself.

An object of the present invention is to make it possible to qualify or further determine an immune material by absorption measurement of an immune complex further easily as compared with fluorescent or luminescent immunoassay.

An immune analysis method according to the present invention includes the steps of mixing a solution containing an antibody or an antigen which is labelled with noble metal colloidal particles with a sample solution to form a sample mixed solution for reacting an antigen or an antibody contained in the sample solution with the labelled antibody or antigen thereby forming a noble metal colloidal labelled immune complex, and employing a cell having a total reflection prism at least on one surface thereof and introducing a measuring beam of a wavelength in a range from visible to infrared regions into the total reflection prism at an angle of incidence causing total reflection thereby measuring absorption of the measuring beam caused at the interface between the total reflection prism and the sample mixed solution. Thus, the antigen or the antibody which is contained in the sample is qualified or further determined.

The noble metal colloid can be prepared from a colloid of gold, silver or copper, and a proper grain size thereof is 5 to 50 nm.

According to the present invention, absorption measurement by the measuring beam can be carried out without separating the antibody or the antigen which is labelled with the noble metal colloid or an unreacted one of the antigen or the antibody contained in the sample solution, thereby implementing homogenous immunoassay analysis. Besides, high sensitive measurement can be implemented by using the noble metal colloid.

An immunoassay apparatus according to the present invention, which is adapted to implement the aforementioned method, comprises a total reflection cell having a total reflection prism consisting of a material having a larger refractive index than the sample mixed solution on at least one of wall surfaces defining a space in which the sample mixed solution is present, an incident optical system for introducing a measuring beam of a wavelength in a range from visible to infrared regions into the total reflection prism at an angle of incidence causing total reflection, and a measuring optical system receiving an outgoing beam from the total reflection prism for measuring absorbance by the sample mixed solution. The absorption in the total reflection is measured from intensity of attenuated total reflection.

The total reflection cell can be formed by a container type cell having only one opening for causing antigen-antibody reaction in the cell for forming a noble metal colloid labelled immune complex or making antigen-antibody reaction in another container for forming a noble metal colloid labelled immune complex and thereafter storing a sample mixed solution containing the noble metal colloid labelled immune complex, or a flow cell having a solution inlet port and a solution outlet port to be fed with a sample mixed solution after formation of a noble metal colloid labelled immune complex.

A light source included in the incident optical system can be formed by that emitting a beam of a continuous wavelength, or a single-wavelength light source such as a laser unit emitting a single-wavelength beam. When the light source emits a continuous wavelength beam, spectrometry can be carried out although the incident or measuring optical system must include a spectroscope. If a single-wavelength light source is employed, on the other hand, absorption measurement only at the single wavelength of the light source is carried out with no requirement for a spectroscope.

When only an antibody or an antigen which is labelled with a noble metal colloid is present in a sample mixed solution which is present in a total reflection cell, no absorption having sensitivity suitable for measurement is recognized. When an immune complex is not labelled with a noble metal colloid, no absorption having sensitivity suitable for measurement is recognized either. Absorption having sensitivity suitable for measurement is recognized at a specific wavelength only when an immune complex which is labelled with a noble metal colloid is present. The feature of the present invention resides in this point, whereby homogeneous immunoassay analysis is enabled.

Assuming that $n_2$ represents the refractive index of a sample mixed solution containing an immune complex and $n_1$ ($n_2 < n_1$) represents the refractive index of a total reflection prism, a critical angle $\theta c$ causing total reflection is expressed as follows:

$$\theta c = \sin^{-1}(n_2/n_1)$$

When a measuring beam into the total reflection prism from an incident optical system is introduced, an angle $\theta$ of incidence (see FIG. 1) upon the interface between the total reflection prism and the sample mixed solution is set at the following condition:

$$\theta > \theta c$$

When homogeneous immunoassay analysis is carried out, a sample mixed solution which is subjected to absorption measurement is a mixed solution containing a noble metal colloid labelled antibody (or antigen), a noble metal colloid labelled immune complex, an unreacted antigen (or antibody), biopolymer and the like.

The measuring beam is that including a continuous wavelength beam in a proper region among near infrared, mid infrared and far infrared regions, or a single-wavelength beam.

Absorption in the total reflection prism is expressed by absorbance A as follows:

$$A = N \cdot \alpha de \cdot \log_{10} e$$

where N represents the number of total reflection times in the total reflection prism, $\alpha$ represents the absorption coefficient of the sample mixed solution, and de represents an optical path length along which the measuring beam penetrates into the sample mixed solution in single total reflection.

According to the present invention, absorption by a noble metal colloid labelled immune complex which is present in a sample mixed solution is measured with a total reflection cell at high sensitivity. Absorption having sensitivity suitable for measurement is measured only in an immune complex which is in a state labelled with a noble metal colloid and no absorption having sensitivity suitable for measurement is recognized in only an antibody or an antigen which is labelled with a noble metal colloid or in an immune complex which is in a state not labelled with a noble metal colloid, whereby qualification and determination of the immune material can be carried out by absorption by total reflection measurement without performing B-F separation, while immunoassay can be carried out through a simple operation and a simple measuring apparatus.

The foregoing and other objects, features, aspects and advantages of the present invention will become more apparent from the following detailed description of the present invention when taken in conjunction with the accompanying drawings.

DESCRIPTION OF THE PREFERRED EMBODIMENTS

Figure 1:
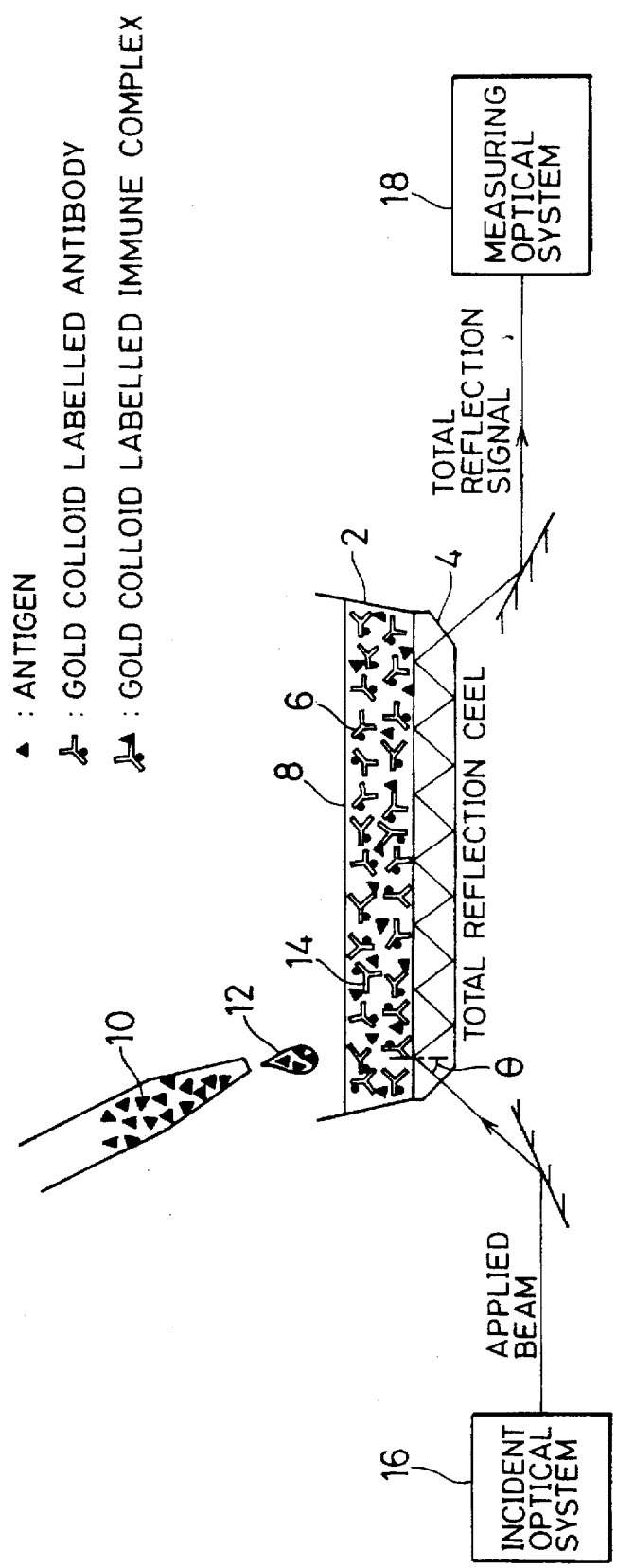
FIG. 1 schematically illustrates an embodiment of the present invention.

FIG. 1 schematically illustrates an embodiment of the present invention. A total reflection cell 2 has a total reflection prism 4 at least on one surface thereof. A mixed solution 8 containing a gold colloid labelled antibody 6 which is adsorbed on a gold colloid serving as an exemplary noble metal colloid is stored in the total reflection cell 2, and a sample solution 12 containing an antigen 10 causing antigen-antibody reaction with the antibody 6 is added thereto, so that the antibody 6 and the antigen 10 make antigen-antibody reaction in the mixed solution 8 stored in the total reflection cell 2, thereby forming a gold colloid labelled immune complex 14. A measuring beam is introduced into the total reflection prism 4 from an incident optical system 16 at an angle θ of incidence causing total reflection, whereby the measuring beam is transmitted through the total reflection prism 4 while being totally reflected, and slightly penetrates into the mixed solution 8 through the interface between the total reflection prism 4 and the mixed solution 8, to be absorbed by the gold colloid labelled immune complex 14 in the mixed solution 8. An outgoing beam from the total reflection prism 4 is received by a measuring optical system 18 so that its absorbance is measured, whereby the antigen 10 contained in the sample solution 12 can be qualified and determined.

Figure 2:
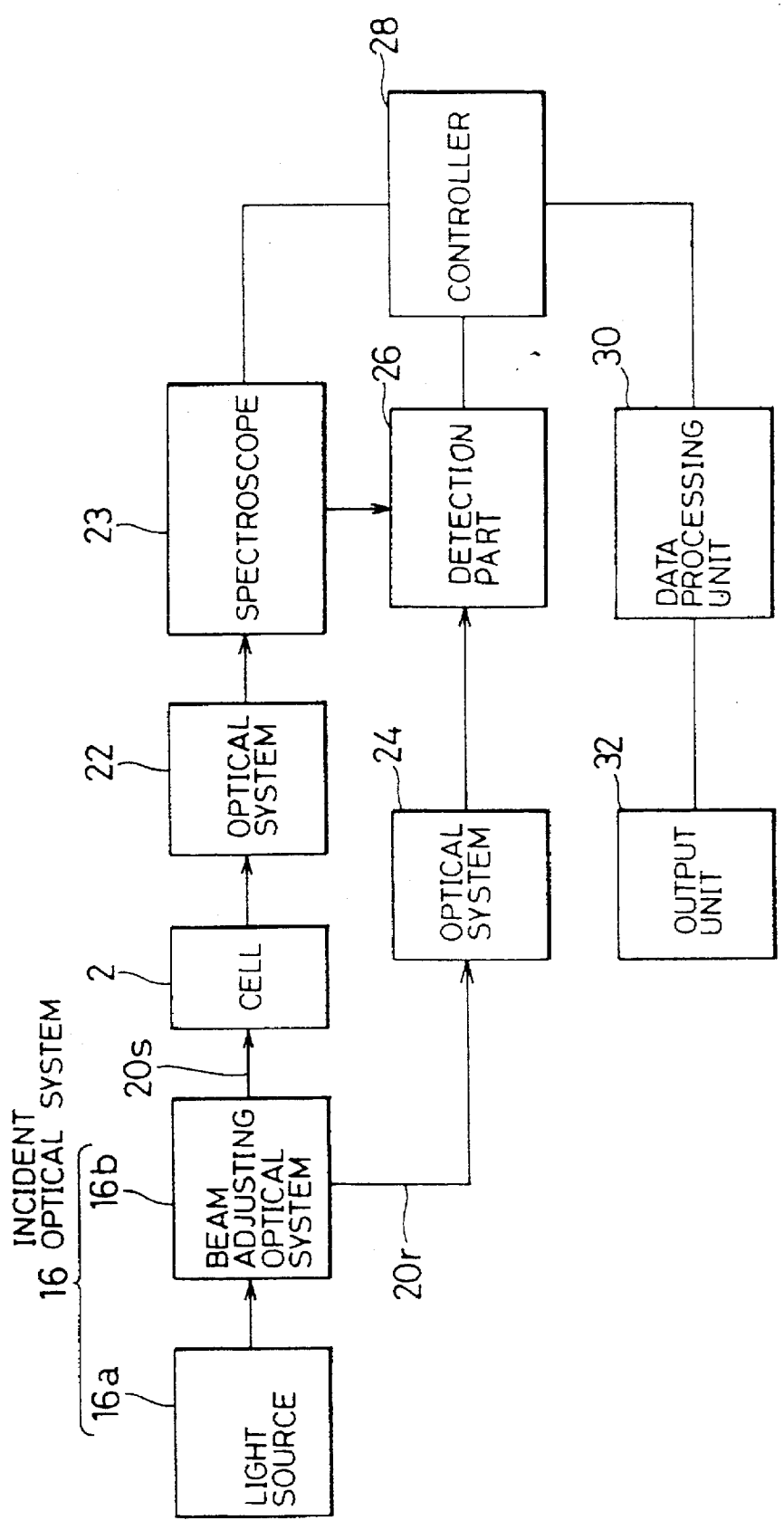
FIG. 2 is a block diagram showing a measuring apparatus according to the embodiment.

FIG. 2 schematically illustrates a measuring apparatus according to the embodiment. The incident optical system 16 includes a light source 16a emitting the measuring beam and a beam adjusting optical system 16b. The beam adjusting optical system 16b includes an optical system for converting the beam from the light source 16a to a parallel beam, a beam splitter for separating the beam into a measuring beam 20s and a reference beam 20r, and an optical system for introducing the measuring beam 20s into the total reflection prism 4 of the total reflection cell 2 at the angle of incidence causing total reflection. An optical system 22 for adjusting the luminous flux of the measuring beam 20s which is totally reflected and transmitted through the total reflection prism 4 of the total reflection cell 2 and a spectroscope 23 for receiving the measuring beam 20s adjusted by the optical system 22 and separating the received measuring beam into its spectral components are arranged on an optical path of the measuring beam 20s, so that the measuring beam 20s which is separated into its spectral components is guided to and detected by a detection part 26. The measuring optical system 18 shown in FIG. 1 includes the optical system 22, the spectroscope 23, and the detection part 26.

On the other hand, an optical system 24 for adjusting the luminous flux of the reference beam 20r is arranged on an optical path of the reference beam 20r for correcting fluctuation of the measuring beam 20s, so that the adjusted reference beam 20r is guided to and detected by the detection part 26. The detection part 26 is so formed as to correct the measuring beam 20s which is transmitted through the total reflection prism 4 and separated into its spectral components through the spectroscope 23 by intensity of the reference beam 20r indicating light source intensity thereby calculating absorbance.

Numeral 28 denotes a controller which controls the spectral operation of the spectroscope 23 for transmitting a detection output from the detection part 26 to a data processor 30. Numeral 32 denotes an output unit such as a recorder or a CRT (cathode-ray tube) outputting the result of processing in the data processor 30.

The light source 16a can be formed by a fluorescent lamp, a xenon lamp, a black-body radiation source, a gas laser, a solid laser or a semiconductor laser.

The material for the total reflection prism 4 can be prepared from ZnSe, Ge, Si, $Al_2O_3$ or MgO. Only the total reflection prism 4 or overall wall surfaces of the total reflection cell 2 including the total reflection prism 4 may be made of such a material.

The spectroscope 23 can be formed by an FTIR (Fourier transformation infrared spectrophotometer), a system which is employing IR-blazed grating and IR-sensitive detector or the like. The spectroscope 23 may be included in the incident optical system 16. When a single-wavelength light source emitting a beam of a single wavelength is employed as the light source 16a, the spectroscope 23 and the controller 28 for controlling the same are unnecessary.

The cell 2 shown in FIG. 1 was employed, the spectroscope 23 of the measuring apparatus shown in FIG. 2 was formed by an FTIR, a ZnSe optical crystal was employed as the total reflection prism 4 of the cell 2, Anti-Mouse IgG (product by BioCell (U.S.A.)) absorbed on a gold colloid of 30 nm in grain size was employed as the noble metal colloid labelled antibody 6, and a mixed solution (pH 7.65) of 0.01 M of TWEEN 21 (polyoxyethyleneaorbitan monolaurate) and PBS (phosphate-buffered saline) was employed as a solvent for a mixed solution containing the antibody 6. Detection was carried out 10 times in a single measuring time of 2 minutes, and the results of the detection were estimated. The spectroscope 23 had a spectral range of 800 to 3200 $cm^{-1}$ and resolution of 2 $cm^{-1}$.

Figure 3:
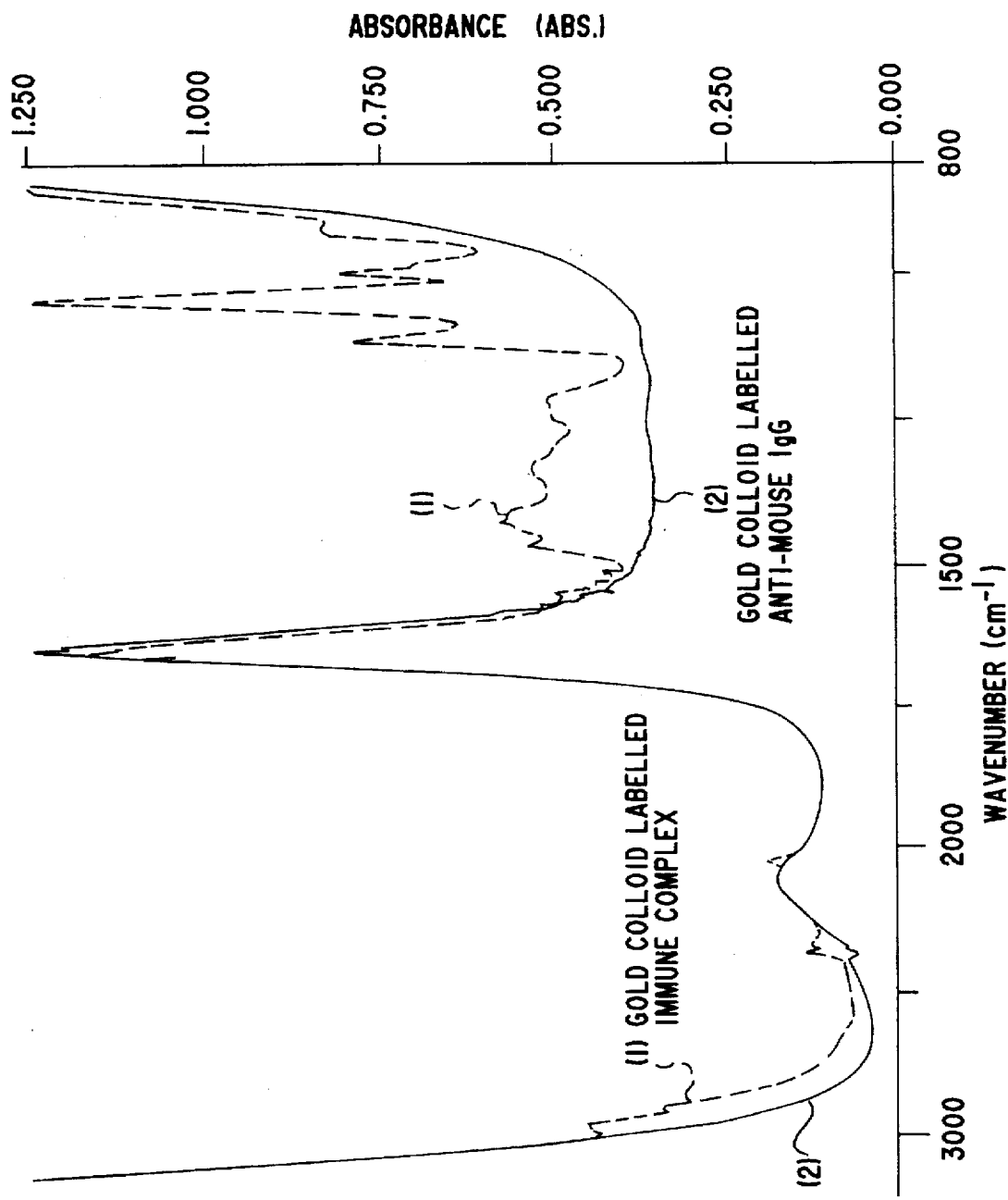
FIG. 3 illustrates spectra of a gold colloid labelled immune complex and a gold colloid labelled antibody in the present invention.
Figure 4:
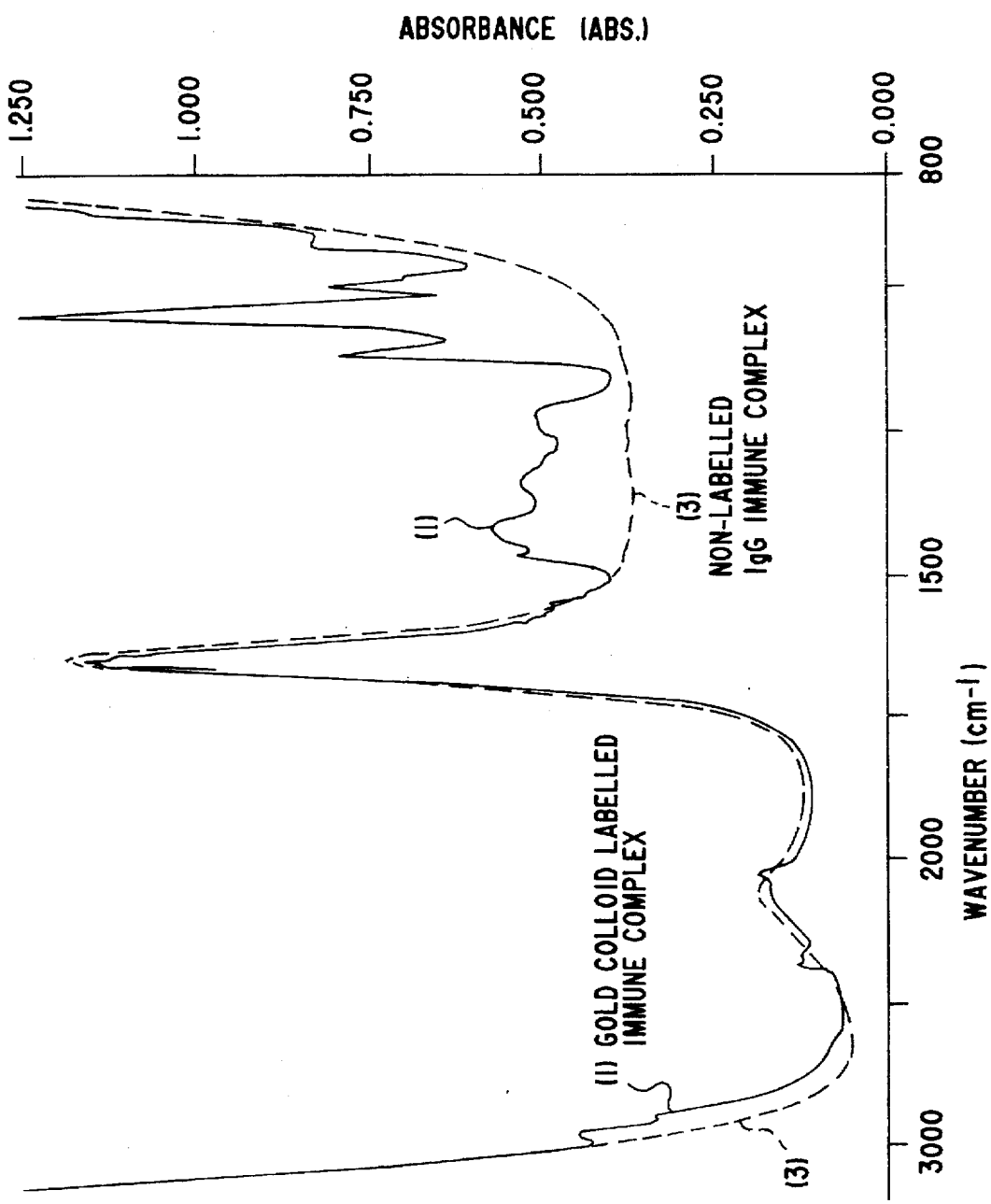
FIG. 4 illustrates spectra of the gold colloid labelled immune complex in the present invention and an immune complex not labelled with a noble metal colloid.

FIGS. 3 and 4 show total reflection spectra of the results of the measurement. Referring to FIG. 3, a spectrum ② is that of a mixed solution containing only the aforementioned 30 nm gold colloid labelled Anti-Mouse IgG. Large absorption is that of water, while no another characteristic absorption is recognized. Referring to FIG. 4, on the other hand, a spectrum ③ is that of a mixed solution of 2 mg/ml in concentration containing only an IgG immune complex not labelled with a noble metal colloid.

No characteristic absorption is recognized in the spectrum ③ either, except that of water. On the other hand, a spectrum ① appearing in each of FIGS. 3 and 4 is that of a mixed solution containing a gold colloid labelled immune complex formed by reaction of 7.5 µg/ml of the aforementioned 30 nm gold colloid labelled Anti-Mouse IgG antibody and 62.5 µg/ml of a Mouse IgG antigen, and characteristic absorption is recognized in addition to that of water.

Figure 5:
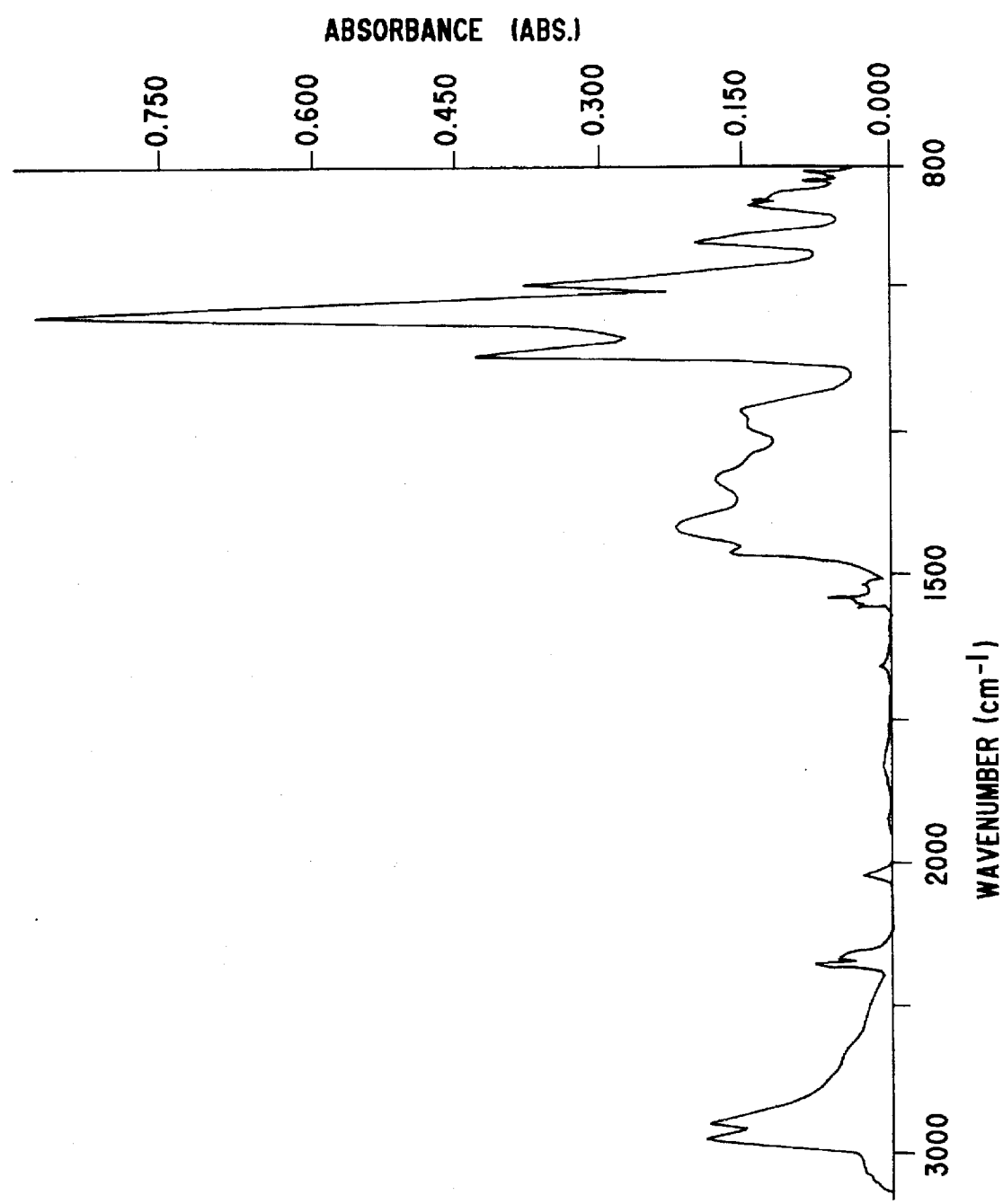
FIG. 5 illustrates a total reflection absorption spectral difference spectrum of the gold colloid labelled immune complex in the present invention based on the spectra shown in FIG. 3.
Figure 6:
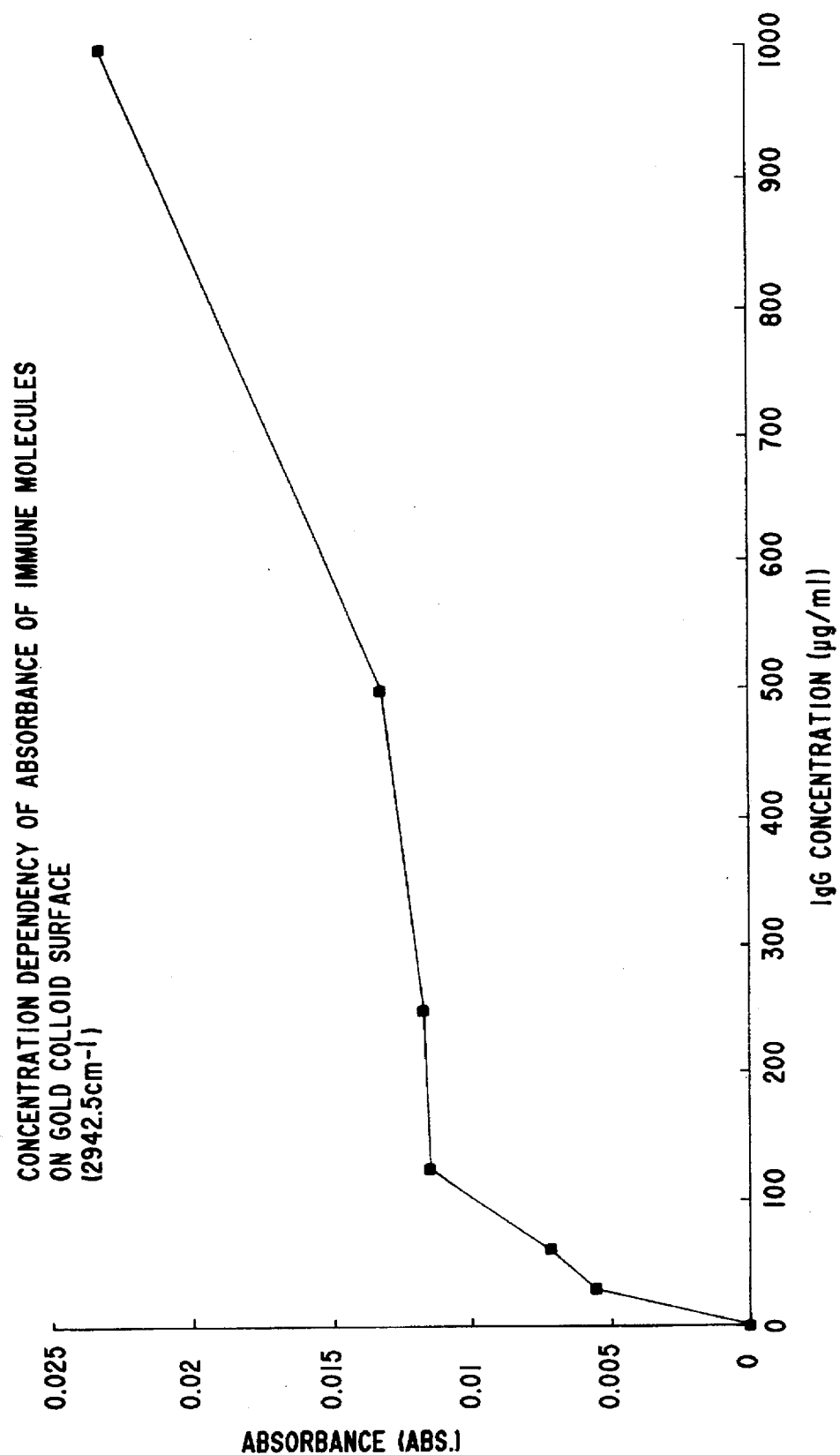
FIG. 6 illustrates concentration dependency of absorbance at 2942.5 $cm^{-1}$ with respect to antibody IgG concentration in the immunoassay method according to the present invention.
Figure 7:
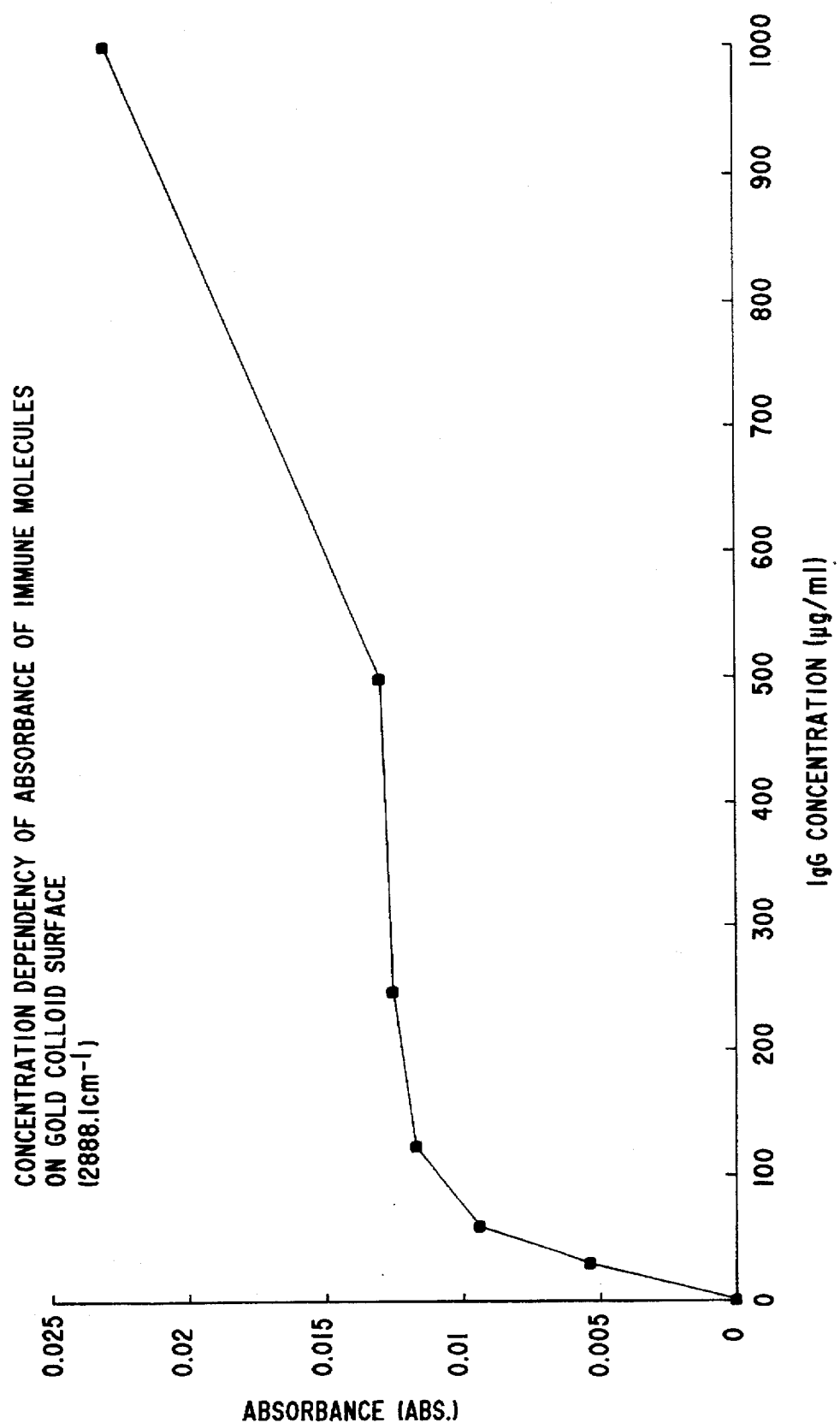
FIG. 7 illustrates concentration dependency of absorbance at 2888.1 $cm^{-1}$ with respect to antibody IgG concentration in the immunoassay method according to the present invention.
Figure 8:
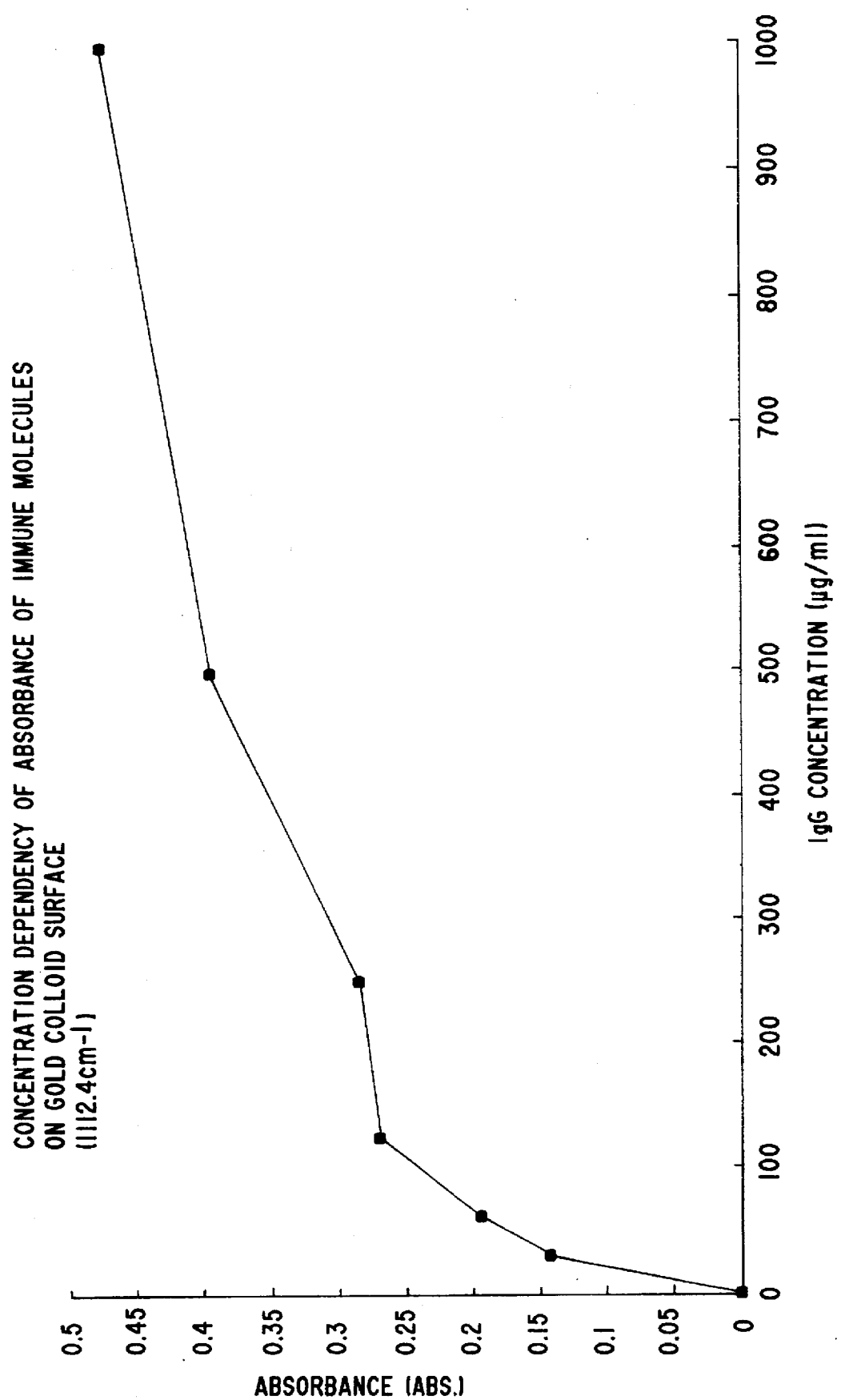
FIG. 8 illustrates concentration dependency of absorbance at 1112.4 $cm^{-1}$ with respect to antibody IgG concentration in the immunoassay method according to the present invention.
Figure 9:
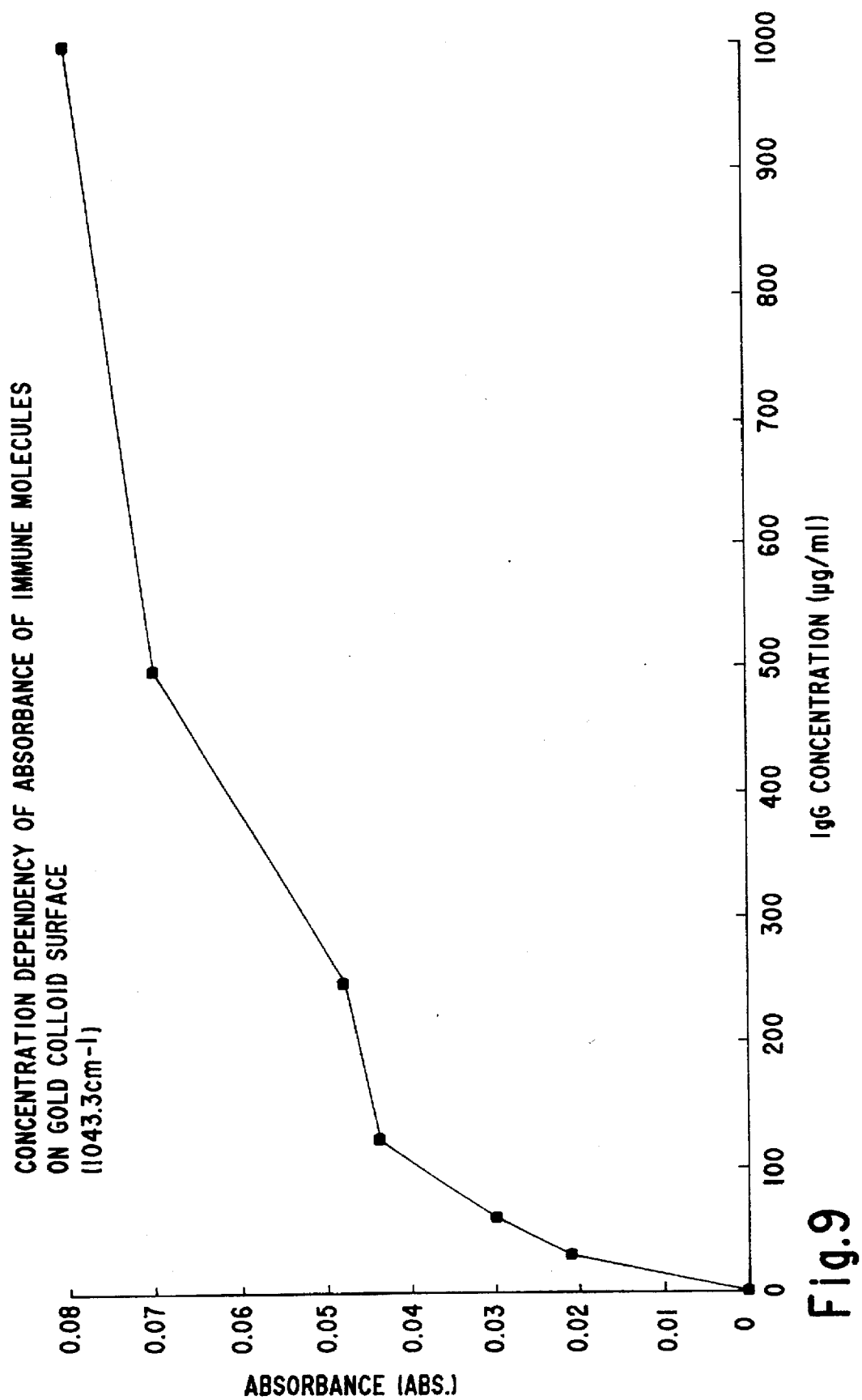
FIG. 9 illustrates concentration dependency of absorbance at 1043.3 $cm^{-1}$ with respect to antibody IgG concentration in the immunoassay method according to the present invention.
Figure 10:
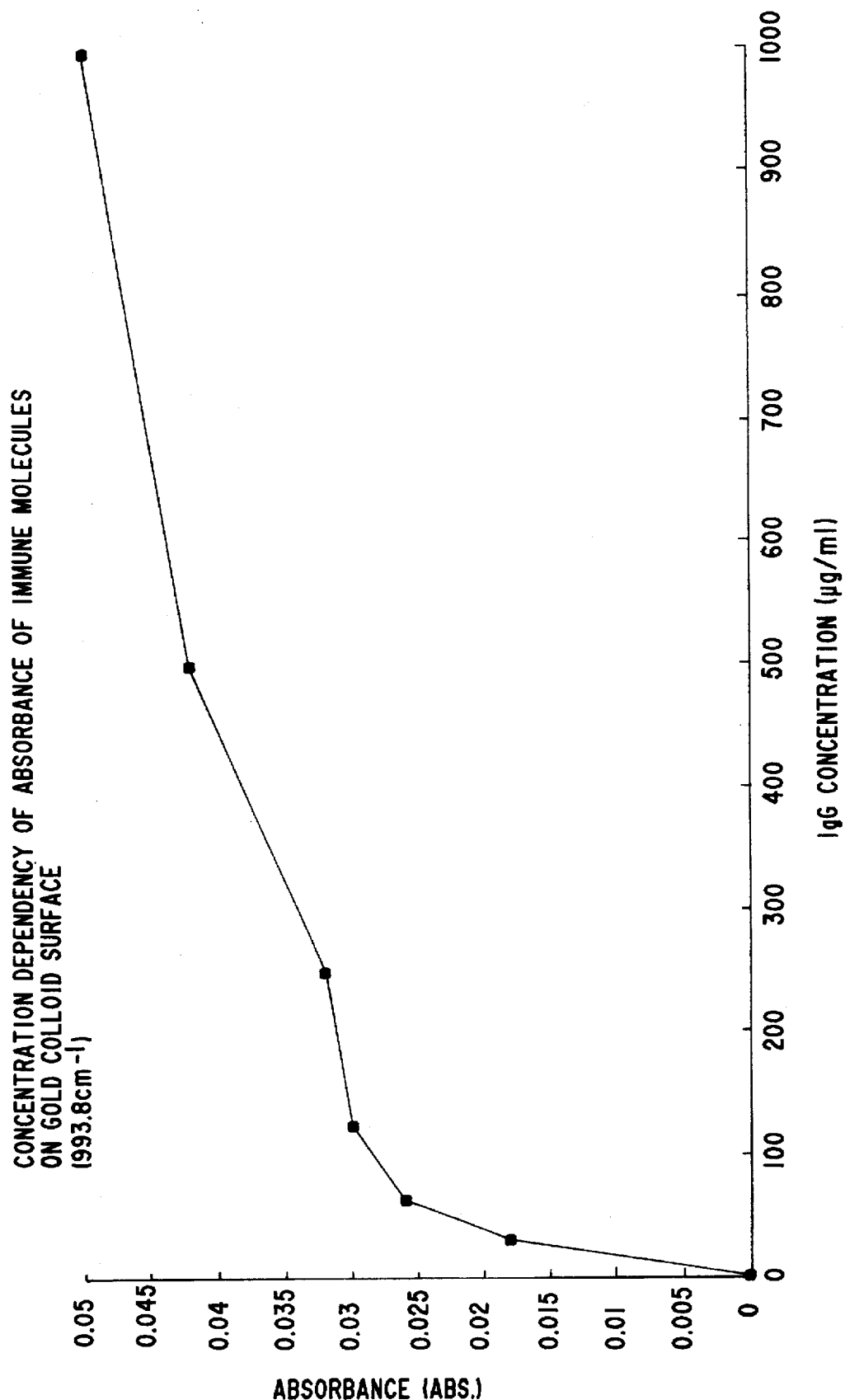
FIG. 10 illustrates concentration dependency of absorbance at 993.8 $cm^{-1}$ with respect to antibody IgG concentration in the immunoassay method according to the present invention.

FIG. 5 illustrates a spectrum obtained by subtracting the spectrum ② from the spectrum a) in FIG. 3 as a background, in order to clearly show the absorption. This spectrum is a total reflection absorption spectral difference spectrum of the gold colloid labelled immune complex formed by reaction of 7.5 µg/ml of the 30 nm gold colloid labelled Anti-Mouse IgG antibody and 62.5 µg/ml of the Mouse IgG antigen. In this spectrum, characteristic absorption bands appear at 2888 $cm^{-1}$ and 2942 $cm^{-1}$ in the vicinity of 2900 $cm^{-1}$, and 993 $cm^{-1}$, 1043 $cm^{-1}$ and 1112 $cm^{-1}$ between the vicinity of 900 $cm^{-1}$ and 1500 $cm^{-1}$, and this is absorption by internal vibration of the IgG immune complex.

FIGS. 6 to 10 illustrate concentration dependency levels of absorbance values at respective wavenumbers of 2942.5 $cm^{-1}$, 2881.1 $cm^{-1}$, 1112.4 $cm^{-1}$, 1043.3 $cm^{-1}$ and 993.8 $cm^{-1}$ as to various concentration values of Mouse IgG antigens reacted with 7.5 µg/ml of 30 nm gold colloid labelled Anti-Mouse IgG antibodies respectively. The axes of abscissas show IgG concentration values, and the axes of ordinates show absorbance values. Every one is saturated in a high concentration region of IgG, while there is a linear relation in a low concentration region, and this shows that quantitative analysis is possible by the inventive method.

Figure 11A:
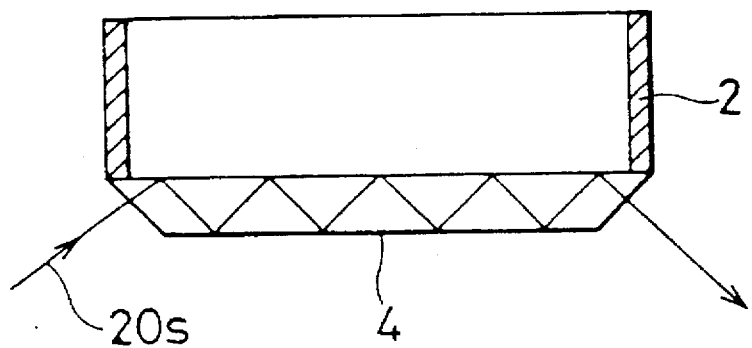
FIG. 11A is a front sectional view showing an exemplary total reflection cell having only one opening.
Figure 11B:
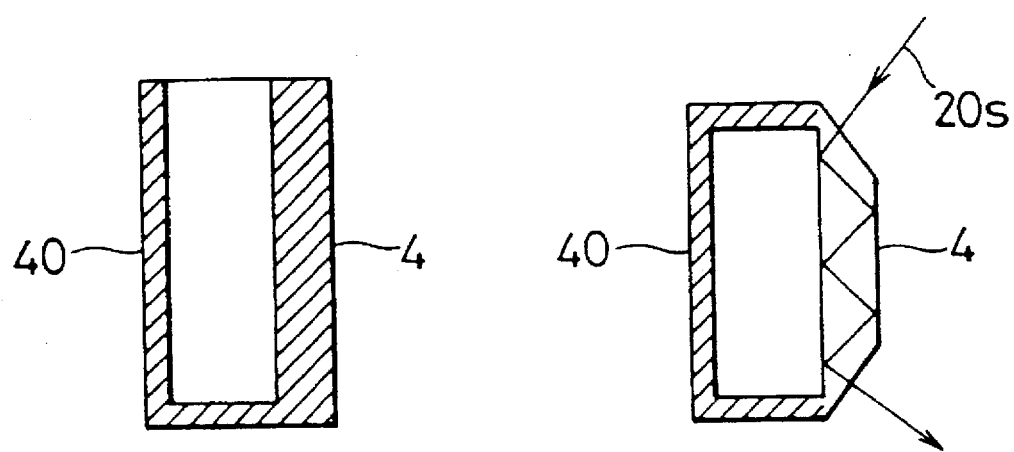
FIG. 11B shows a front sectional view and a plan view illustrating another total reflection cell having only one opening respectively.

FIGS. 11A and 11B show exemplary total reflection cells having only single openings. FIG. 11A illustrates the cell 2 shown in FIG. 1, having the total reflection prism 4 on its bottom surface.

FIG. 11B shows a front sectional view and a top plan view of a cell 40 having a total reflection prism 4 on its side surface.

FIGS. 12A to 12E show perspective views and front sectional views of cells having other shapes respectively.

Figure 12A:
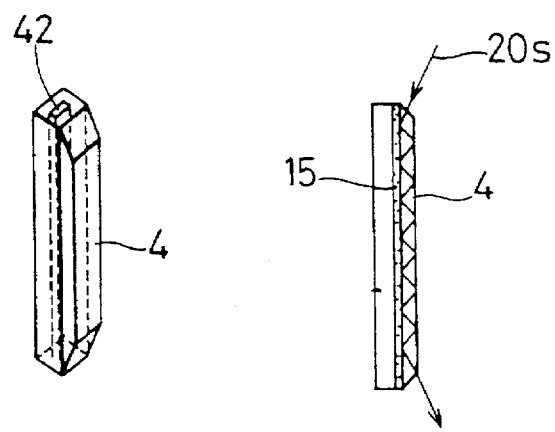
FIG. 12A is a perspective view and front sectional view showing illustrates an exemplary throwaway total reflection cell.

FIG. 12A shows a single-sided throwaway cell, which is provided with a narrow clearance 42 for sucking a sample mixed solution by a capillary phenomenon and a total reflection prism 4 formed along the clearance 42. Numeral 15 denotes the sample mixed solution which is sucked in the clearance 42.

Figure 12B:
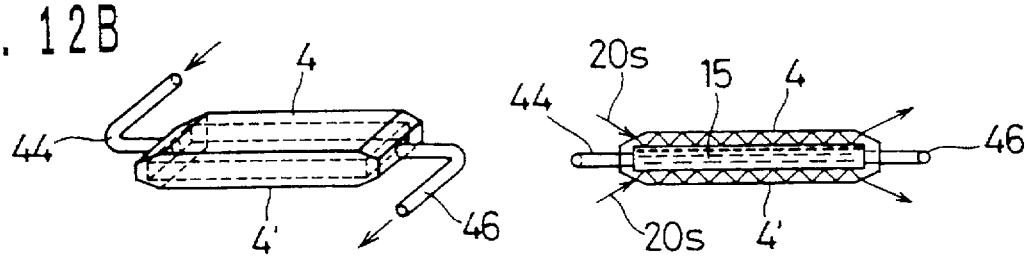
FIGS. 12B to 12E are perspective views and front sectional views showing other exemplary total reflection flow cells respectively.

FIG. 12B shows an exemplary double-sided total reflection flow cell, which is provided on upper and lower surfaces thereof with total reflection prisms 4 and 4' through a space fed with a sample mixed solution. Numeral 44 denotes a sample mixed solution inlet port for the cell, and numeral 46 denotes a sample mixed solution outlet port from the cell.

Figure 12C:
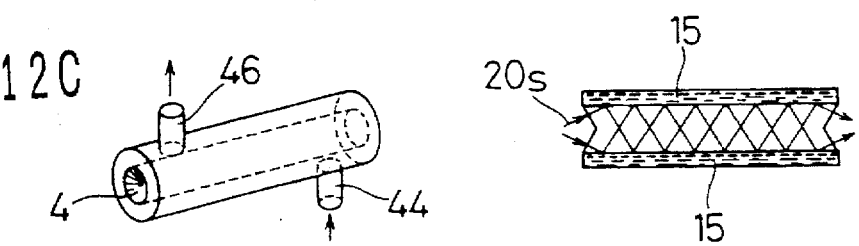

FIG. 12C shows an exemplary cylindrical total reflection flow cell, which is formed to enclose a side surface of a cylindrical total reflection prism 4. A sample mixed solution 15 is fed along the cylindrical surface of the total reflection prism 4.

Figure 12D:
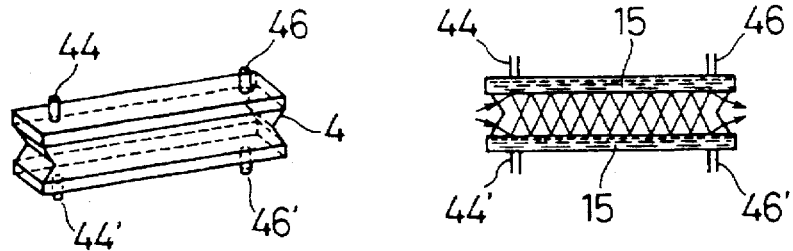

FIG. 12D shows another exemplary double-sided total reflection flow cell, which is so formed that a sample mixed solution 15 is fed along two opposite surfaces of a total reflection prism 4 respectively.

Figure 12E:
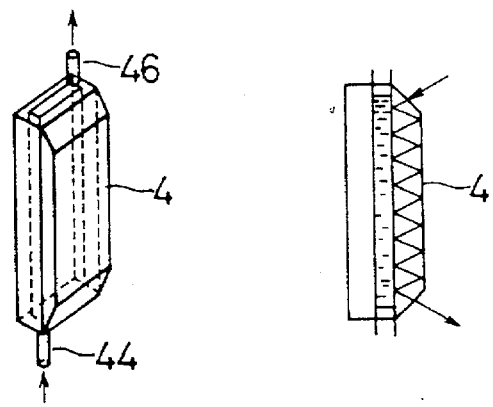

FIG. 12E shows an exemplary single-sided total reflection flow cell, having a total reflection prism 4 on one surface defining a space fed with a sample mixed solution 15.

Although the present invention has been described and illustrated in detail, it is clearly understood that the same is by way of illustration and example only and is not to be taken by way of limitation, the spirit and scope of the present invention being limited only by the terms of the appended claims.

We claim:

1. A method for quantitatively determining a target antigen or a target antibody in a liquid sample in an immunoassay, comprising:

(a) reacting said liquid sample with a solution comprising an antibody or antigen labelled with a colloidal noble metal particle, wherein said antibody or antigen specifically binds to said target antigen or said target antibody, respectively, to form a liquid sample/solution mixture containing a labelled immune complex;

(b) contacting said liquid sample/solution mixture with a total reflection cell having a surface comprising a total reflection prism;

(c) illuminating said total reflection prism with a measuring beam of light having a wavelength in a range of visible to infrared light at an angle of incidence which causes total reflection at an interface between said total reflection prism and said liquid sample/solution mixture in said total reflection cell;

(d) measuring absorption of said measuring beam at the interface; and (e) comparing said measured absorption to a standard absorption obtained from a known concentration of said target antigen or said target antibody processed according to steps (a)–(d) to determine the amount of said target antigen or said target antibody in said liquid sample.

2. The method in accordance with claim 1, wherein said reacting step (a) is carried out in said total reflection cell.

3. The method in accordance with claim 1, wherein said reacting step (a) is carried out in a reaction container, and said liquid sample/solution mixture is thereafter transferred into said total reflection cell in said contacting step (b).

4. The method in accordance with claim 1, wherein said colloidal noble metal particle label is a colloidal gold, silver or copper particle label.

5. A method for qualitatively determining a target antigen or a target antibody in a liquid sample in an immunoassay, comprising:

(a) reacting said liquid sample with a solution comprising an antibody or antigen labelled with a colloidal noble metal particle, wherein said antibody or antigen specifically binds to said target antigen or said target antibody, respectively, to form a liquid sample/solution mixture containing a labelled immune complex;

(b) contacting said liquid sample/solution mixture with a total reflection cell having a surface comprising a total reflection prism;

(c) illuminating said total reflection prism with a measuring beam of light having a wavelength in a range of visible to infrared light at an angle of incidence which causes total reflection at an interface between said total reflection prism and said liquid sample/solution mixture in said total reflection cell; and (d) measuring absorption of said measuring beam at the interface to determine the presence of said target antigen or said target antibody in said liquid sample.

* * * * *